United States Patent [19]

Meilland, deceased

[11] Patent Number: Plant 6,791

[45] Date of Patent: May 9, 1989

[54] ROSE PLANT—MEIBARKE VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 134,457

[22] Filed: Dec. 14, 1987

[30] Foreign Application Priority Data

Dec. 12, 1986 [DE] Fed. Rep. of Germany ..... ROS 583

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Burns, Doane, Swecker & Mathis

[57] ABSTRACT

A new and distinct variety of rose plant of the Miniature Class is provided which forms in abundance highly attractive bicolored semi-double blossoms. The blossoms are whitish in coloration and are suffused at the margins with cardinal pink. The plant is very low and dense and reflowers well. It is particularly well suited for use as attractive ornamentation when grown as a flowering pot plant either indoors or outdoors.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the Meigurami variety. The male parent (i.e., the pollen parent) of the new variety was the MAGIC CARROUSEL variety (U.S. Plant Pat. No. 3,601). The parentage of the new variety can be summarized as follows:

MEIGURAMI×MAGIC CARROUSEL.

The seeds resulting from the above pollination were sown and 33 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive semi-double bicolored blossoms which are whitish in coloration and are suffused at wide margins with cardinal pink,
(b) exhibits a bushy growth habit, and
(c) forms a very low and dense plant.

The new variety well meets the needs of the horticultural industry for many usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meibarke variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years old and observed during September while grafted on *Rosa froebelii* outdoors at Cannet-des-Maures, Var, France.

DETAILED DESCRIPTION

Figures 1, 2, 3, 4, 5, 6, 7, 8, 9, 10, 11, 12, 13, 14, 15, 16, 17:
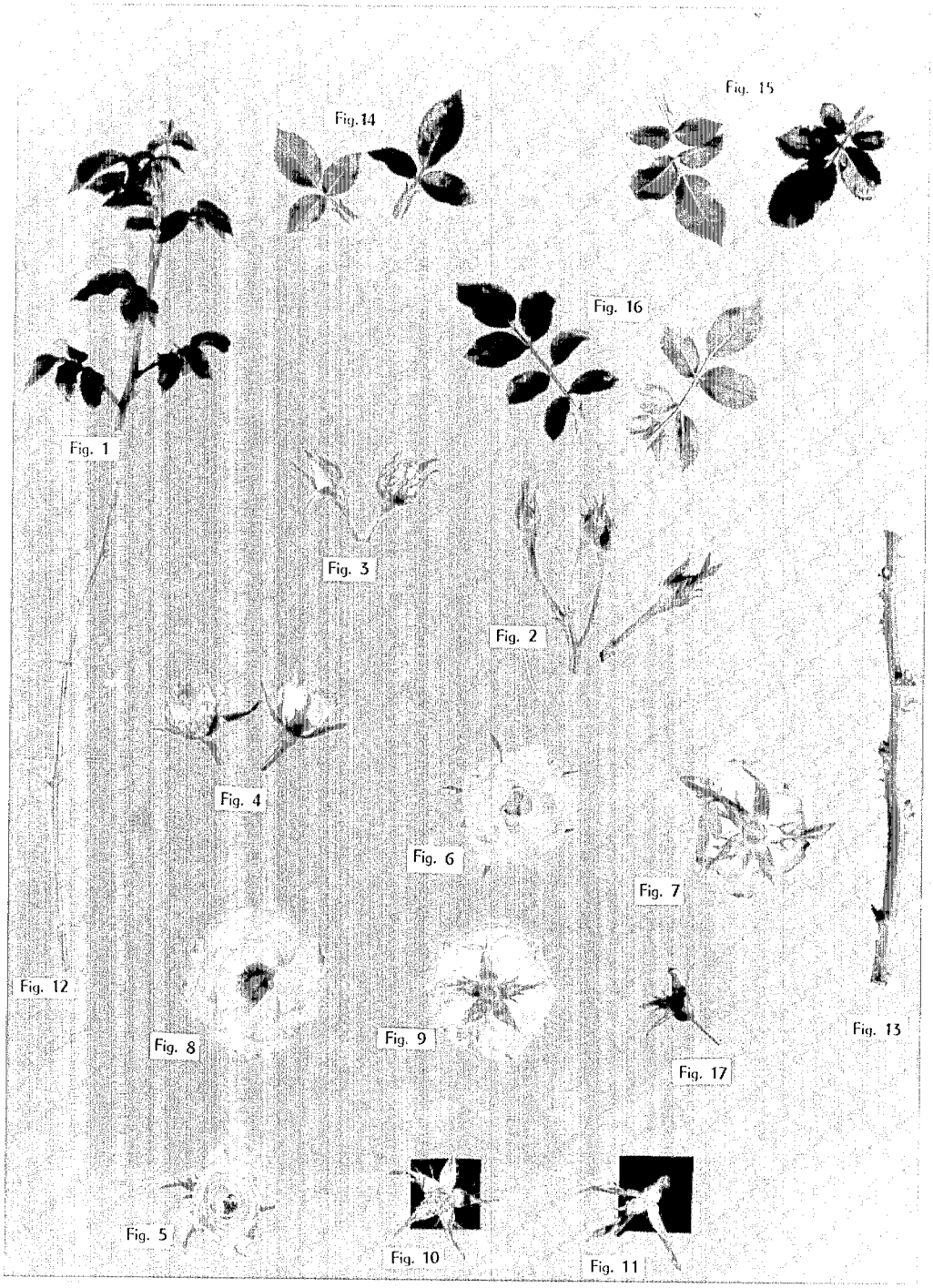
FIG. 1 illustrates a specimen of a young shoot.
FIG. 2 illustrates a specimen of four floral buds before the opening of the sepals.
FIG. 3 illustrates a specimen of a pair of floral buds at the opening of the sepals.
FIG. 4 illustrates a specimen of a pair of floral buds at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown on the right and the under surface being shown on the left.
FIG. 15 illustrates specimens of leaves with five leaflets with the upper surface being shown on the right and the under surface being shown on the left.
FIG. 16 illustrates specimens of leaves with seven leaflets with the upper surface being shown on the left and the under surface being shown on the right.

The chart used in the identification of the colors is that of the Royal Horticultural Society (R.H.S. Colour Chart). The description is based on two year old specimens of the new variety during September while growing outdoors when grafted on *Rose frobelii* at Cannet-des-Maures, Var, France, Class: Miniature.

Plant:

*Height.*—Approximately 40 to 45 cm. on average.

*Habit.*—Bushy.

Branches:

*Color.*—Young stems: light green, Yellow-Green Group 146C, widely shaded with a reddish tint. Adult wood: medium green, Yellow-Green Group 146B.

Leaves:

*Petioles.*—Upper surface: grooved, reddish brown on young foliage and medium green on adult foliage with glandular edges. Under surface: light green with some thorns.

*Stipules.*—Adnate, pectinate, very wide and linear.

*Leaflets.*—Number: 3, 5 (most often), and 7. Shape: oval with lance-shaped point. Serration: simple and regular. Texture: leathery. General appearance: dense and semi-glossy. Color (young foliage): upper surface: reddish brown. under surface; reddish brown. Color (adult foliage): Upper surface: dark green, Yellow-Green Group 147A. Under surface: medium green, Yellow-Green Group 147B.

Inflorescence:

*Number of flowers.*—Approximately 1 to 9 per stem.

*Peduncle.*—Medium green, straight, rigid, more or less shaded with a reddish tint, it bears reddish glandular aciculas, its length is approximately 2 cm. on average.

*Sepals.*—Upper surface: tormentose, greenish colored with a reddish tint. Under surface: light green, more of less shaded with reddish coloration, has more or less glandular edges. The outside sepals have edges which are more or less appendiculated.

*Buds.*—Shape: oval. Length: approximately 1.5 cm. on average. Size: small. Color upon opening: upper surface: light orange yellow, widely edged with cardinal pink of Red Group 53B and suffused with light cardinal pink of Red Group 53C. under surface: similar to upper surface.

*Flower.*—Form: as a flattened cup. Diameter: approximately 4.5 cm. on average. Color (when opening begins): upper surface: light orange yellow widely edged with cardinal pink of Red Group 53B and suffused with light cardinal pink of Red Group 53C. Under surface: similar to upper surface. Color (when blooming): upper surface: whitish tint suffused at the margins with cardinal pink of Red Group 53B. Under surface: similar to upper surface. Color (at end of opening): Upper surface: whitish tint suffused at the margins with cardinal pink of Red Group 53B. Under surface: similar to upper surface. Fragrance: none. Lasting quality: long. Petal number: approximately 20 on average. Petal form: generally round. Petal texture: firm. Petal drop: the petals drop off cleanly. Anthers: normal, bright yellow. Stamen number: approximately 93 to 98 on average. Filaments: yellowish of irregular heights, Pistil number: approximately 35 to 38 on average. Stigmas: normal, straw colored. Style: greenish with a fuchsine tip, of irregular heights. Receptacle: light green at the dehiscence of the anthers and in longitudinal section is in the shape of a jug.

Development:

*Vegetation.*—Vigorous.

*Blooming.*—Abundant and continuous.

*Aptitude to bear fruit.*—Normal.

*Resistance to frost.*—Good.

*Resistance to disease.*—Good.

I claim:

1. A new and distinct variety of Miniature rose plant characterized by the following combination of characteristics:

(a) forms in abundance on a continuous basis attractive semi-double bicolored blossoms which are whitish in coloration and are suffused at wide margins with cardinal pink, (b) exhibits a bushy growth habit, and (c) forms a very low and dense plant;

substantially as herein shown and described, together with the parts thereof.

* * * * *